(12) United States Patent
Fang et al.

(10) Patent No.: US 11,896,360 B2
(45) Date of Patent: Feb. 13, 2024

(54) SYSTEMS AND METHODS FOR GENERATING THIN IMAGE SLICES FROM THICK IMAGE SLICES

(71) Applicants: LVIS Corporation, Palo Alto, CA (US); THE BOARD OF TRUSTEES OF THE LELAND STANFORD JUNIOR UNIVERSITY, Stanford, CA (US)

(72) Inventors: Zhongnan Fang, Santa Clara, CA (US); Akshay S. Chaudhari, Stanford, CA (US); Jin Hyung Lee, Palo Alto, CA (US); Brian A. Hargreaves, Stanford, CA (US)

(73) Assignee: LVIS Corporation, Palo Alto, CA (US)

( * ) Notice: Subject to any disclaimer, the term of this patent is extended or adjusted under 35 U.S.C. 154(b) by 700 days.

(21) Appl. No.: 16/979,104

(22) PCT Filed: Mar. 12, 2019

(86) PCT No.: PCT/US2019/021903
§ 371 (c)(1),
(2) Date: Sep. 8, 2020

(87) PCT Pub. No.: WO2019/178133
PCT Pub. Date: Sep. 19, 2019

(65) Prior Publication Data
US 2020/0397334 A1  Dec. 24, 2020

Related U.S. Application Data

(60) Provisional application No. 62/641,836, filed on Mar. 12, 2018.

(51) Int. Cl.
*A61B 5/055* (2006.01)
*G16H 50/70* (2018.01)
(Continued)

(52) U.S. Cl.
CPC ............ *A61B 5/055* (2013.01); *A61B 5/7267* (2013.01); *G06N 3/045* (2023.01); *G06T 15/00* (2013.01);
(Continued)

(58) Field of Classification Search
CPC ... A61B 5/055; A61B 5/7267; A61B 2576/00; A61B 5/0033; A61B 6/03; A61B 5/7264;
(Continued)

(56) References Cited

U.S. PATENT DOCUMENTS

| 5,432,544 A | 7/1995 | Ziarati |
| 2010/0183217 A1* | 7/2010 | Seung ............... G06T 5/001 |
| | | 382/156 |

(Continued)

FOREIGN PATENT DOCUMENTS

| JP | 2017091529 A | 5/2017 |
| WO | 2017091833 A1 | 6/2017 |
| WO | 2019178133 A1 | 9/2019 |

OTHER PUBLICATIONS

International Search Report and Written Opinion dated May 24, 2019 for PCT Application No. PCT/US2019/021903.
(Continued)

*Primary Examiner* — Nimesh Patel
(74) *Attorney, Agent, or Firm* — Dorsey & Whitney LLP

(57) ABSTRACT

Systems and methods for generating thin slice images from thick slice images are disclosed herein. In some examples, a deep learning system may calculate a residual from a thick slice image and add the residual to the thick slice image to generate a thin slice image. In some examples, the deep learning system includes a neural network. In some examples, the neural network may include one or more levels, where one or more of the levels include one or more blocks. In some examples, each level includes a convolution
(Continued)

block and a non-linear activation function block. The levels of the neural network may be in a cascaded arrangement in some examples.

24 Claims, 11 Drawing Sheets

(51) Int. Cl.
    *A61B 5/00*     (2006.01)
    *G06T 15/00*     (2011.01)
    *G06N 3/045*     (2023.01)

(52) U.S. Cl.
CPC ... *G16H 50/70* (2018.01); *G06T 2207/30004* (2013.01)

(58) Field of Classification Search
CPC ........ A61B 6/501; G06N 3/045; G06N 3/048; G06N 3/08; G06N 3/084; G06N 3/082; G06N 3/047; G06N 3/04; G06N 20/00; G06N 3/0464; G06N 3/049; G06N 3/088; G06T 15/00; G06T 2207/30004; G06T 2207/10072; G06T 2207/10136; G06T 2207/20081; G06T 2207/20084; G06T 3/4053; G06T 5/003; G06T 2207/10088; G06T 5/50; G06T 2207/20132; G06T 7/11; G06T 2207/20221; G06T 2207/10036; G06T 2207/20172; G06T 17/00; G06T 2207/30196; G06T 7/32; G06T 3/4046; G06T 7/0012; G06T 2207/10081; G06T 5/002; G06T 5/001; G06T 7/73; G06T 2207/30096; G06T 2207/20216; G06T 2207/20224; G16H 50/70; G16H 30/40; G16H 50/20; G16H 30/00; G16H 30/20; G16H 10/60; G16H 80/00; G16H 10/20; G16H 10/40; G16H 50/30; G16H 70/60; G06F 18/214; G06F 18/253; G06F 18/22; G06F 30/20; G06F 18/24765; G06F 9/4806; G06F 18/241; G06F 18/2415; G06F 18/24; G06F 18/2137; G06F 18/25; G06V 10/20; G06V 40/16; G06V 10/247; G06V 10/30; G06V 10/40; G06V 10/765; G06V 10/774; G06V 10/806; G06V 10/82; G06V 20/46; G06V 20/52; G06V 40/103; G06V 40/168; G06V 40/172; G06V 40/23; G06V 2201/03; G06V 40/193; G06V 40/197; G06V 10/761; G06V 10/764; G06V 10/771; G06V 10/7715; G06V 10/80; G06V 20/64; G06V 40/10; G06V 40/165; Y02A 90/10
See application file for complete search history.

(56) References Cited

U.S. PATENT DOCUMENTS

2016/0196672  A1    7/2016  Chertok et al.
2019/0108634  A1*  4/2019  Zaharchuk ............... G06T 5/50
2020/0065940  A1*  2/2020  Tang ................. G06F 18/214

OTHER PUBLICATIONS

Oktay, Ozan et al., "Multi-Input Cardiac Image Super-Resolution using Convolutional Neural Networks", MICCAI 2016: Medical Image Computing and Computer-Assisted Intervention, 2016, pp. 246-254.
Extended European Search Reported for EP Application 19767141.5, dated Nov. 9, 2021.
Lim, Bee , et al., "Enhanced Deep Residual Networks for Single Image Super-Resolution", Department of ECE, ASRI, Seoul National University, 08826, Seoul, Korea, Jul. 10, 2017, pp. 1-9.
Oktay, Ozan , et al., "Multi-input Cardiac Image Super-Resolution Using Convolutional Neural Networks", Biomedical Image Analysis Group, Imperial College London Institute of Clinical Science, Imperial College London, London DOI: 10.1007/978-3-319-46726-9_29, Oct. 2, 2016, pp. 1-9.
Yu, Haichao , et al., "Computed Tomography Super-Resolution Using Convolutional Neural Networks", Beckman Institute, University of Illinois at Urbana-Champaign Department of Computer Science and Engineering, Texas A&M University Jump Trading Simulation and Education Center b University of Illinois College of Medicine, Sep. 17, 2017, pp. 3944-3948.
Zhao, Can , et al., "Self Super-Resolution for Magnetic Resonance Images Using Deep Networks", Dept. of Electrical and Computer Engineering, The Johns Hopkins University Dept. of Computer Science, The Johns Hopkins University, Feb. 26, 2018, pp. 1-4.
"Office Action for IL Appl. No. 277035, dated Jun. 26, 2023; 4 pages".
"Office Action for CA 3,092,994, dated Sep. 29, 2023 pgs. all".
"Office Action and Translation for JP 2020-548680, dated Apr. 19, 2023".
Yu, Haichao, et al., Computed tomography super—resolution using convolutional neural networks, 2017 IEEE International Conference on Image Processing (ICIP), IEEE, 2017, pp. 3944-3948, https://ieeexplore.ieee.org/stamp/stamp.jsp?tp=&arnumber=8297022.
"Decision on Refusal for JP Appl. No. 2020-548680, dated Nov. 8, 2023".

* cited by examiner

SYSTEMS AND METHODS FOR GENERATING THIN IMAGE SLICES FROM THICK IMAGE SLICES

CROSS-REFERENCE TO RELATED APPLICATION

This application is a 35 U.S.C. § 371 National Stage Application of PCT Application No. PCT/US2019/021903, filed Mar. 12, 2019, which claims the benefit under 35 U.S.C. § 119 of the earlier filing date of earlier filed U.S. Provisional Application No. 62/641,836 filed on Mar. 12, 2018, the entire contents of which are hereby incorporated by reference in their entirety, for any purposes.

STATEMENT AS TO RIGHTS TO INVENTIONS MADE UNDER FEDERALLY SPONSORED RESEARCH OR DEVELOPMENT

This invention was made with government support under contract grant numbers NIH R01 AR063643 and R01 EB002524 awarded by the National Institutes of Health (NIH). The government has certain rights in the invention.

TECHNICAL FIELD

Examples described herein relate generally to processing image slices from a three dimensional images. More specifically, examples described herein relate to processing thick image slices from three dimensional images to generate thin slices for the three dimensional images. The thin slices may be analyzed, viewed, or otherwise used to diagnose and/or treat disease in some examples.

BACKGROUND

In three-dimensional (3D) imaging modalities, such as magnetic resonance imaging (MRI), computed tomography (CT), positron emission tomography (PET), and ultrasound (US), volumes are imaged as a series of imaging planes (e.g., slices) with finite thicknesses (e.g., 0.5 mm, 1 mm, 0.5 cm, 1 cm). The slices are combined to generate a 3D image of the volume where each voxel of the 3D image corresponds to a portion of the imaged volume. The resolution of the 3D image may be based, at least in part, on a magnitude of the volume represented by each voxel. The greater the volume represented by a voxel, the lower the acquire more slices within the volume. That is, the thickness of the slices is reduced and the volume represented by each voxel is reduced. For example, a volume imaged as a series of 0.5 mm slices may produce a higher resolution 3D image than when the volume is imaged as a series of 1.0 mm slices.

Higher resolution images may provide more information to observers than low resolution images. For example, clinicians may be able to make more accurate diagnoses from medical images with higher resolution compared to those with lower resolution. However, it may not be feasible to acquire thinner slices of a volume in some applications. For example, some imaging systems may be limited to a minimum slice thickness that cannot be reduced. In some applications, acquiring thinner slices may require additional imaging time. This may reduce patient comfort, for example, when the patient must remain in a confined space for a longer period of time and/or must hold their breath during acquisition of the slices. With some imaging modalities, acquiring thinner slices may require additional exposure to ionizing radiation which may increase health risks to the patient.

Accordingly, there is a need to improve resolution of 3D images without decreasing the thickness of slices acquired during imaging.

SUMMARY

Examples of technology described herein may provide a super-resolution technique using a deep learning system for generating thin-slice 3D images (e.g. MRI, fMRI, PET, US, and/or CT) from thicker input slices, and to compare this method to alternative through-plane interpolation methods.

In accordance with some examples of the present disclosure, a deep learning system including a 3D convolutional neural network is described, which is configured to learn residual-based transformations between high-resolution thin-slice images and lower resolution thick-slice images. In some examples, the neural network is trained to learn residual-based transformations between high-resolution thin-slice images and lower-resolution thick-slice images at the same center locations. While 3D musculoskeletal MR images are provided as an example this method can be generally applied to any 3D images and to the imaging of any area of the human or animal body including brain, liver, cardiovascular systems, etc.

A neural network, such as a 3D convolutional neural network, in accordance with principles of the present disclosure may be capable of resolving high-resolution thin-slice MRI from lower-resolution thicker slices. The neural network may achieve superior quantitative and qualitative diagnostic performance to both conventionally utilized and state-of-the-art methods for MR, CT, and/or other 3D imaging modalities while reducing the number of slices required to be acquired in some applications.

A method of generating thin slice images from thick slice images according to an example of the present disclosure may include receiving a first image having a first resolution at a neural network, performing a convolution on the first image with the neural network, performing a non-linear activation function on the first image with the neural network, repeating the convolution and non-linear activation function, generating a residual based on another convolution with the neural network, and summing the residual and the first image with the neural network to generate a second image having a second resolution, wherein the second resolution is higher than the first resolution.

A system for generating thin slice images from thick slices images according to an example of the present disclosure may include a non-transitory computer readable medium including instructions for implementing a neural network, wherein the neural network comprises a level including a convolution block and a rectified linear unit non-linear activation block, wherein the level is configured to generate a residual from a first image having a first resolution received by the neural network, wherein the neural network is configured to sum the first image and the residual to generate a second image having a second resolution, wherein the second resolution is higher than the first resolution, and a processor configured to execute the instructions to implement the neural network A system for generating high resolution images from low resolution images according to an example of the present disclosure may include an image acquisition unit configured to acquire a first image of a feature of interest at a first resolution, a computing system configured to implement a deep learning system, wherein the deep learning system is configured to receive the first image of the feature of interest and, based at least in part on the first image, generate a second image of the feature of interest at a second resolution, wherein the second resolution is higher than the first resolution, and a display configured to display the second image of the feature of interest.

DETAILED DESCRIPTION

Figure 1:
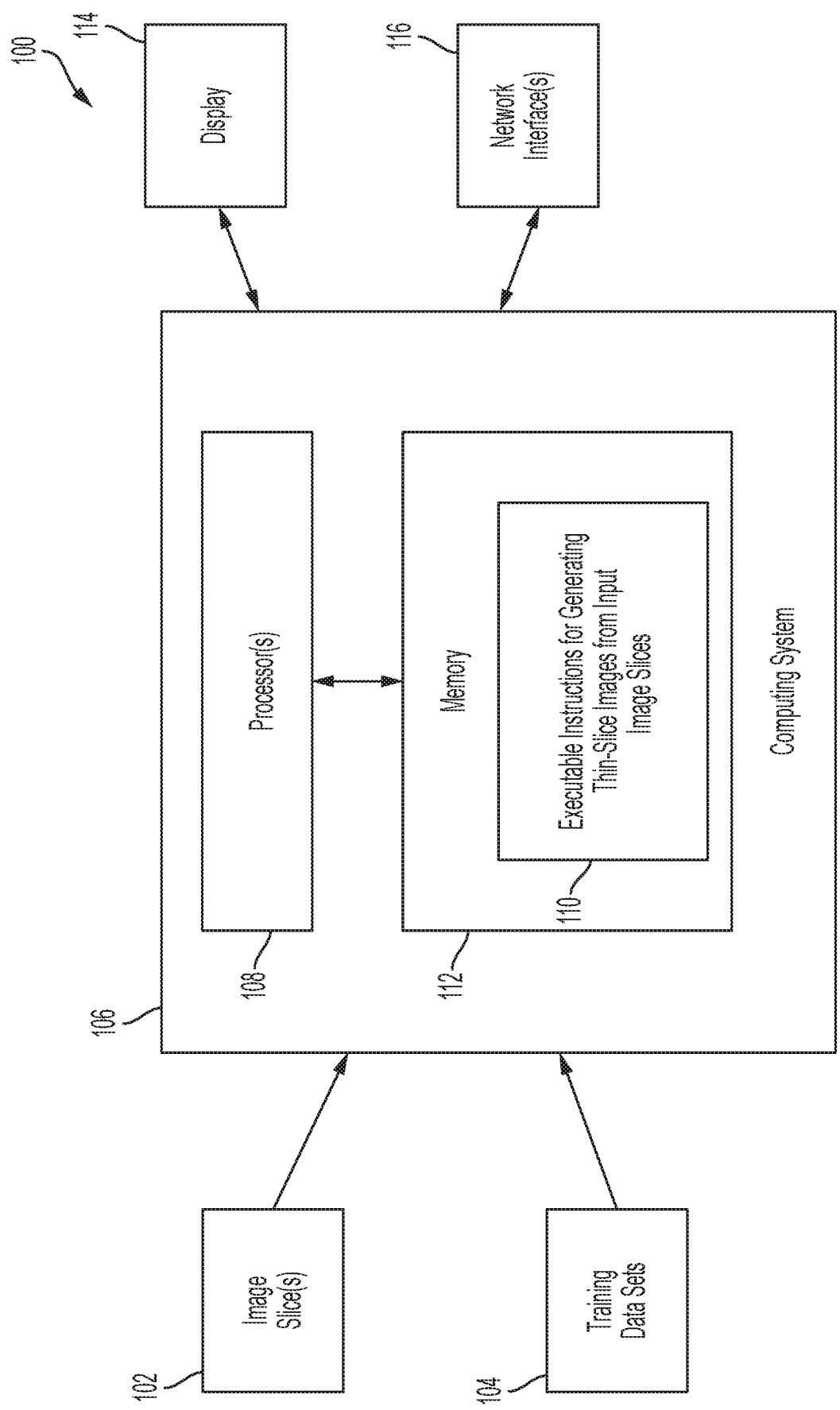
FIG. 1 is a block diagram of a system arranged in accordance with examples described herein.

Certain details are set forth below to provide a sufficient understanding of described embodiments. However, it will be clear to one skilled in the art that embodiments may be practiced without these particular details. In some instances, well-known brain imaging techniques and systems, circuits, control signals, timing protocols, and/or software operations have not been shown in detail in order to avoid unnecessarily obscuring the described embodiments.

Rapid acquisition of high-resolution 3D medical images with adequate signal-to-noise ratio is challenging due to hardware limitations in modalities such as magnetic resonance imaging (MRI), functional magnetic resonance imaging (fMRI), positron emission tomography (PET) and computed tomography (CT).

In MRI, clinical musculoskeletal imaging protocols typically include 2D fast-spin-echo (FSE) sequences scanned in various scan planes, often with the same contrast. While such sequences provide excellent in-plane resolution, there is always an associated risk for missing subtle lesions due to partial volume effects in slices with a high section thickness (usually 2.5-4 mm) and with slice gaps. Image acquisitions with thick slices also preclude image reformations into arbitrary scan planes, which makes it challenging to interrogate tissues with oblique orientations, such as the anterior cruciate ligament and the articular cartilage of the femoral trochlea for example.

Several methods have been proposed recently for thin-section musculoskeletal MRI, with 3D fast spin-echo (using vendor products SPACE, CUBE, or VISTA) being a popular choice. However, 3D FSE sequences typically compromise in-plane resolution for through-plane resolution and suffer from substantial echo train blurring despite the use of variable flip angle methods. Consequently, despite acquiring thin-section images, the overall diagnostic quality of 3D FSE remains limited. 3D radial sequences have been used for isotropic musculoskeletal imaging but have not seen widespread adoption likely due to a different artifact appearance. Besides sequence-based approaches, compressed sensing (CS) and parallel imaging are also promising methods for accelerating thin-section MRI, however, neither is an ideal stand-alone method. CS MRI is uncommon in 2D FSE clinical protocols because only one dimension can be used to generate incoherent sampling, in addition to long reconstruction times. Parallel imaging acceleration is ultimately limited by SNR and g-factor. Additionally, the geometries of common knee coils (such as rigid 8-channel) are ill-suited for acceleration in all directions.

Single image super-resolution, an active field in image processing, can potentially boost MRI spatial resolution to generate thin-section MRI without compromising SNR or requiring additional MRI hardware or scan time. Interpolation, for example, is one naive implementation of super-resolution. With the practical acquisition challenges for thin-section imaging, MRI vendors offer retrospective interpolation of slices using zero-padded Fourier interpolations (FI) through options such as 'ZIP2' and 'Interpolate' for GE Healthcare and Siemens Healthineers MRI scanners, respectively. Similarly, medical image viewing platforms such as OsiriX use trilinear interpolation during image manipulation and multi-planar reformation of data. Low-order linear interpolation methods such as FI and trilinear interpolation are widely used in clinical and research protocols for attempting to achieve thin-section imaging, however, neither produce images with high diagnostic quality.

Besides interpolation, another primary method of MRI super-resolution imaging entails utilizing image sparsity with only single images required as inputs. The current state-of-the-art MRI single-image super-resolution algorithm is based on sparse-coding super-resolution (ScSR), which was initially developed for natural images, but later adapted to a handful of MRI applications. While promising, this super-resolution method has not been pervasive in medical imaging due to limited resolution improvements and slow execution speeds for 3D data.

According to principles of the present disclosure, a deep learning system may be configured to apply super-resolution techniques used with natural 2D images to 3D medical images. In some examples, the deep learning system may be implemented using artificial intelligence systems, machine learning systems, neural networks (e.g., convolutional neural networks), and/or other computational technologies. In some examples, a software-based post-processing neural network may at least partially overcome the limitation of 3D medical imaging just described. The neural network may be a convolutional neural network in some examples. The neural network may employ deep-learning techniques in some examples. Because images are used to train and deploy the neural network, the neural network is independent of the image acquisition hardware platform.

Examples describing musculoskeletal MRI will be will be used to explain the architecture of the deep learning system and how it is trained and implemented. However, the deep learning system can be generally applied to different 3D medical images including MRI, fMRI, PET, and CT. The application areas are not limited to musculoskeletal imaging and includes images that cover any areas such as brain, liver, and cardiovascular systems.

Examples described include systems for using deep-learning with MRI super-resolution for generating thin-slice images and maintaining high in-plane resolution to reduce overall scan time. As used herein, "thick" and "thin" are used as relative terms. That is, slices referred to as "thick" have a dimension in at least one dimension (e.g., elevational, azimuthal, lateral) that is greater than a dimension of a "thin" image in the corresponding dimension. The resolution of an image generated by a slice may be based on a magnitude of a volume represented by a voxel in the image. The greater the volume represented by a voxel, the lower the resolution of the image. An image generated from a thick slice may have more volume associated with each voxel than an image generated from a thin slice. The proposed deep learning systems and methods may be referred to as 'Deep-Resolve' as it helps resolve high-resolution features from low-resolution inputs. DeepResolve may include a convolutional neural network for deep-learning (e.g., machine learning). Specifically, examples described herein train a neural network using publicly available datasets to generate high-resolution thin-slice knee MR images from slices at the same locations but with 2-8 times higher slice thickness. The deep learning system may not necessarily generate identical images to the ground truth; rather, in some applications, the deep learning system may enhance low-resolution images to make them more similar to the ground-truth (e.g., high resolution images) as compared to commonly-utilized and state-of-the art methods. This may enhance the diagnostic value of images acquired from thick-slices in some applications.

FIG. 1 is a schematic illustration of a system arranged in accordance with examples described herein. The system 100 includes image slices (e.g., thick slices) 102, training data sets 104, computing system 106, processor(s) 108, executable instructions for generating thin-slice from input image slices 110 (also referred to herein simply as executable instructions), memory 112, display 114, and network interface(s) 116. Additional, fewer, and/or other components may be used in other examples. In some examples, some or all of the components of the system 100 may be included with an imaging system. For example, the computing system 106 may be included in an imaging system. For example, an MRI, CT, and/or ultrasound imaging system.

The image slices 102 and/or training data sets 104 may be provided by an imaging system. In some examples, the image slices 102 and/or training data sets 104 may be provided by multiple imaging systems. The imaging systems may be of the same modality or different modalities. The image slices 102 and/or training data sets 104 may be stored in a memory accessible to the computing system 106 and/or transmitted to the computing system 106 (e.g., using wired or wireless communication). The computing system 106 may be configured to generate a deep learning system based on the training data sets 104. The deep learning system may include one or more functions for generating thin slice images from image slices 102. The functions may be generated and/or optimized based on the training data sets 104.

The training data sets 104 may train the deep learning system to find a difference (e.g., residual) between a thick slice image and a corresponding thin slice image. After training, the deep learning system may generate a thin slice image from an input image slice 102 by applying the functions to the image slice 102. The functions may supplement the image slice 102 to generate a thin slice (e.g., high resolution) image. In some examples, the deep learning system may calculate a difference between an input image slice 102 and a desired high resolution image (e.g., thin slice image) and add the difference to the input image slice 102 to generate a high resolution image. In some examples, the deep learning system may include one or more neural networks. One or more of the neural networks may be a convolutional neural network in some examples. One or more of the neural networks may include multiple layers, where each layer includes one or more functions or portions of functions for generating thin slice images from the image slices 102.

The computing system 106 may be configured to generate thin-slice (e.g., higher resolution) images from the image slices 102 with the deep learning system generated from the training data sets 104. In some examples, the memory 112 may be encoded with executable instructions 110 for deep learning system that is configured to generate thin-slice images based on thick slice 102 inputs. In some examples, the deep learning system may be partially or wholly implemented in hardware (e.g., ASIC, FPGA). In some examples, the executable instructions 110 may include instructions in a hardware description language (e.g., VHDL) which may be used to design hardware to implement some or all of the deep learning system.

Examples described herein may utilize computing systems, which may generally include hardware and/or software for implementing a deep learning system for generating thin-slice images. For example, the computing system 106 may include one or more processor(s) 108. The processor(s) 108 may be implemented, for example, using one or more central processing units (CPUs), graphical processing units (GPUs), application-specific integrated circuits (ASICs), field programmable gate arrays (FPGA), or other processor circuitry. In some examples, the processor(s) 108 may execute some or all of the executable instructions 110. The processor(s) 108 may be in communication with memory 112. The memory 112 may generally be implemented by any computer readable media (e.g., read-only memory (ROM), random access memory (RAM), flash, solid state drive, etc.). While a single memory 112 is shown, any number may be used, and they may be integrated with the processor(s) 108 in a single computing system 106 and/or located within another computing system and in communication with processor(s) 108.

In some examples, the system 100 may include display 114, which may be in communication with computing system 106 (e.g., using a wired and/or wireless connection), or the display 114 may be integrated with the computing system 106. The display 114 may display one or more image slices 102 and/or one or more thin slices generated by the computing system 106. Any number or variety of displays may be present, including one or more LED, LCD, plasma, or other display devices.

In some examples, the system 100 may include network interface(s) 116. The network interface(s) 116 may provide a communication interface to any network (e.g., LAN, WAN, Internet). The network interface(s) 116 may be implemented using a wired and/or wireless interface (e.g., Wi-Fi, BlueTooth, HDMI, USB, etc.). The network interface(s) 116 may communicate data which may include image slices 102 and/or thin slice images generated by the deep learning system implemented by the computing system 106.

Figure 2:
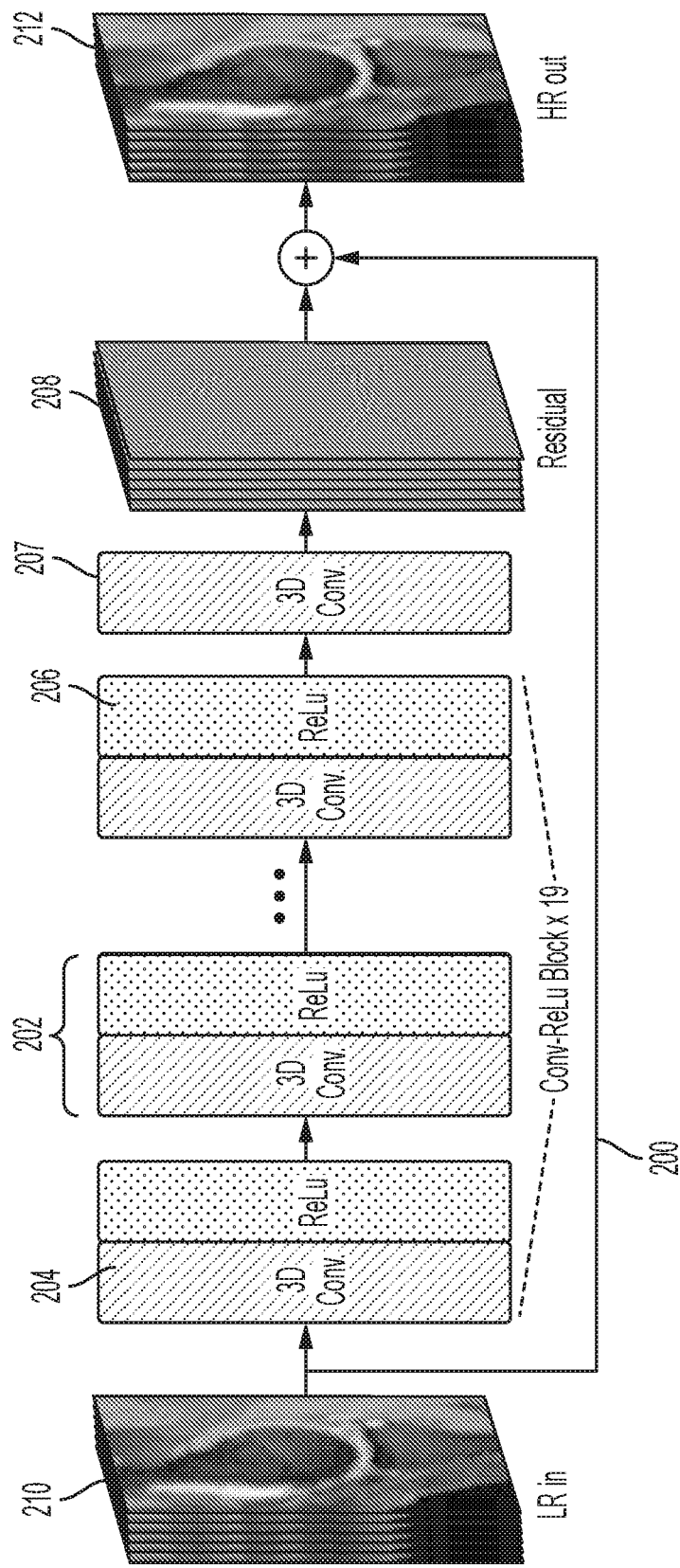
FIG. 2 is an illustration of a neural network arranged in accordance with examples described herein.
Figure 3:
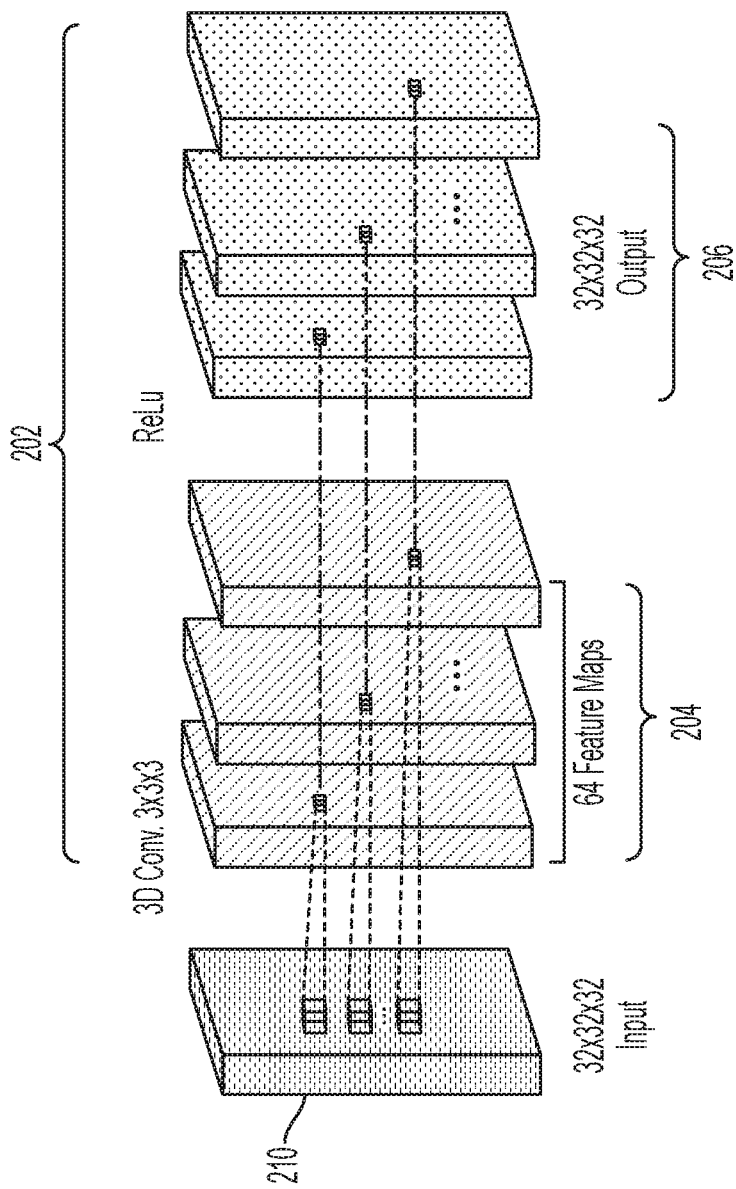
FIG. 3 is an illustration of a portion of the neural network shown in FIG. 2.
Figure 4:
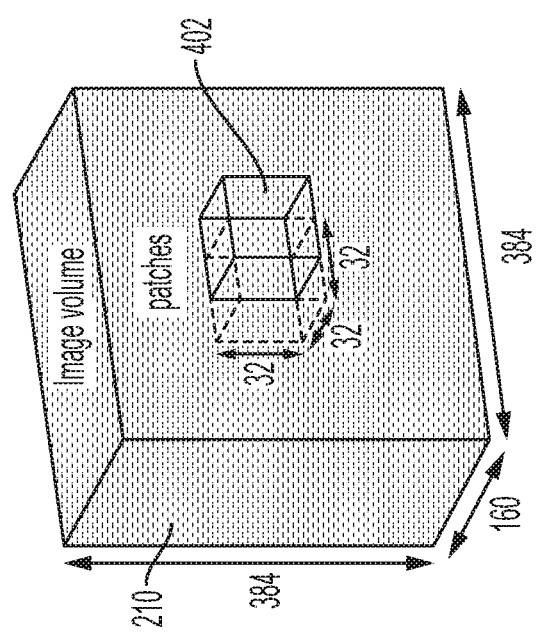
FIG. 4 is an illustration a portion of the neural network shown in FIGS. 2 and 3.

With reference to FIGS. 2-4, an example deep learning system will be described. During training, a set of i ground-truth high-resolution thin-slice images $X_h^i$ and corresponding low-resolution thick-slice images interpolated to the thin-slice locations $X_l^i$, with the same field of view and matrix size may be provided as a training set. The deep learning system may include one or more functions. In the example implementation, the deep learning system includes a function $f=f(X_l)$ that calculates a residual difference image $r^i$ between the ground-truth and interpolated low-resolution images ($r^i = X_h^i - X_l^i$). This function may be trained by optimizing (with an L2-loss):

$$\operatorname*{argmin}_{f} \|r^i - f(X_l^i)\|_2^2. \tag{1}$$

In the implemented examples described herein, an L2 loss function is used for optimizing the deep learning system. Additional loss functions such as the L1-norm, pSNR, SSIM, and/or any other metrics measuring image differences could be used in other examples. Other optimizing functions may be used in other examples.

The deep learning system may be an unsupervised learning algorithm in some examples. The function generated and/or optimized by training, such as the function in Equation (1), may be implemented in one or more neural networks which may have multiple layers in some examples. The function may be implemented across multiple layers of a neural network in some examples. Each layer of the neural network may include one or more blocks. Each block may implement at least a portion of the function. In some examples, each layer of the neural network includes the same blocks (e.g., the blocks repeat in each layer), but in other examples, layers of the neural network may include different blocks.

In an example implementation, a deep learning system may be modeled as a cascade of convolutional filters. As illustrated in FIG. 2, each level (e.g., layer) 202 of deep learning system 200 may include a convolutional block 204 and a rectified linear unit non-linear activation function block (ReLu) 206, which will be described in more detail later on. The deep learning system 200 may compute a residual (e.g., residual image) 208 from an input low-resolution (LR) image 210 (e.g., thick slice image) in order to generate the corresponding high-resolution (HR) image 212 (e.g., thin slice image). While 2D convolutions may be used, deep learning system may utilize 3D convolutions that can provide additional spatial information to improve super-resolution performance.

After the deep learning system has been trained, the estimated residual $f(X_l^i)$ can be calculated directly and a high-resolution super-resolution image $\widetilde{X}_{sr}^i$ (e.g., generated thin slice image) can be generated through $$\widetilde{X}_{sr}^i = X_l^i + f(X_l^i). \tag{2}$$

The implemented example of the deep learning system includes a neural network with 19 layers of paired convolution 204 and rectified linear unit (ReLU) non-linear activation function blocks 206 (e.g., activation function), and an additional layer including a convolution block 207. However, other numbers of layers may be used in other examples. The input LR image 210 may pass through a first layer and processed by the convolution block 204 and ReLu block 206. The processed input image may then be passed as an input to the convolution block 204 and ReLu block 206 of the next layer. This process repeats until the input LR image 210 has been processed by all of the layers of the neural network and the residual 208 is output.

As illustrated in FIG. 3, the filter size of the first and last layer of the neural network of the implemented example of the deep learning system has dimensions of 32×32×32×1 while all other layers have dimensions of 32×32×32×64, where the first 3 numbers represent the x, y, z spatial dimensions and the last number represents the number of filters (also referred to as number of filter channels). The final layer may not include an activation function to ensure that the generated residual includes positive and negative values. However, in other examples, the activation function may be included in the final layer. Continuing this example, as illustrated in FIG. 4, during training of the neural network, each input LR image 210 of the 3D data set is divided into isotropic 32×32×32 pixel patches 402, and all patches from all training data set images are used during the training process. During the application phase (e.g., when the trained neural network is used to generate thin slice images), the input image may not necessarily be divided into patches.

In some examples, the one or more layers of the deep learning system may be trained to identify one or more features. Different layers may identify different features in some examples. The feature recognition may be used as part of optimizing the functions generated for each layer. The features may be in the form of feature maps in some examples. As previously mentioned, the example deep learning system is implemented using a cascade of convolutional filters paired with non-linear activations functions. In the convolutional block 204, the input images (32×32-32 pixel patches) may be convolved with multiple (e.g., 64) 3-dimensional filters with dimensions of 3×3×3, stride of 1×1×1. Consequently, in the first neural network layer, the input patch was transformed into feature maps with dimensions of 32×32×32×64. Subsequent layers maintained identical dimensions except in the final layer where feature reduction was performed to generate a residual image of dimensions 32×32×32. Convolutions were performed on a zero-padded input and the output was cropped to the size of the original input in order to maintain identical input and output dimensions. Other filter arrangements may be used in other examples. For example, different sized input patches may be used as well as different sized feature maps. Other feature reduction and/or padding methods may be performed based, at least in part, on dimensions of input images and desired dimensions of output images.

Continuing with the example implementation, in the ReLU block 206, the non-linear activation functions of the form $R(x)=\max(0,x)$ is used for ensuring that the feature map outputs are non-linear representations of the input. The input low-resolution patch is transformed through a cascade of convolutional and ReLU pairs 202, except for the final layer 207 that generated the residual image of size 32×32×32. The final (20th) convolutional layer in this example did not include a ReLU activation to ensure that the residual image could include positive and negative values. However, in other examples, the final layer may include a ReLU activation block 206. The residual image 208 is added to the input image to generate an approximate high-resolution image. In some examples, the mean-square-error L2-loss may be compared to the original high-resolution image to evaluate the training. If the mean-square-error L2-loss is unacceptably high, the deep learning system may require additional training and/or additional or fewer layers may be added to the deep learning system in addition to further training.

In the example implementation, a small convolution filter size of 3×3×3 is used in the deep learning system which may avoid averaging together high frequency image and convolutional details. Filters with larger supports can be effectively decomposed into several smaller filters, introducing unnecessary redundancy during the network training process. As a result, a small convolution kernel may efficiently improve and/or maximize high-resolution feature extraction. In some examples, a pooling layer may be utilized, but it may average together high-resolution details. However, this may be desirable in some applications for memory optimization. One or more of the feature maps may be zero-padded prior to convolutions and cropped to the original input-size following the convolutions in order to maintain equivalent patch-input and convolution-output sizes in some examples. This may ensure the details at the edges of patches maintain fidelity. Moreover, patches may overlap in some examples. For example, a patch overlap of 50% of the patch size may be used during the deep learning system training phase. However, in some examples, the testing data may be divided into large patches without overlap to mitigate network effects caused at patch edges.

The example implementation of the deep learning system has a depth of 20. The depth may be chosen based, at least in part, on the convolution filter and image patch sizes used. For example, after the first 3×3×3 convolution, the receptive field for each weight in the second layer is 3×3×3. After the second 3×3×3 convolution, the total receptive field for the next weight is 5×5×5, which can be generalized to $(2D+1)^3$, where D is the current network depth. Thus, for a patch size of 32×32×32, the receptive field for a weight in the 16th layer corresponds to features encountered in the entire image patch. Additional deeper layers may provide even higher-level abstractions. Since super-resolution is by nature an ill-posed problem, providing spatial cues at varying length-scales by adding additional layers may Careful optimization may be useful given the high-dimensionality of the deep learning system and hyperparameter space. Increasing the depth of the deep learning system may improve super-resolution quality. Moreover, deep-learning models may follow a power-law loss relationship, which may help determine ideal training data size.

Referring back to FIG. 1, the training described with reference to FIGS. 2-4 may be implemented by processor(s) 108 of computing system 106 based on the training data sets 104. The processor 108 may generate executable instructions 110 to implement the deep learning system as described in reference to FIGS. 2-4 and store the executable instructions 110 on a memory 112 of the computing system 106. The processor 108 may then execute the stored executable instructions 110 to implement the deep learning system. Once the executable instructions 110 have been stored, the executable instructions 110 may be transferred to another computing system. That is, once the deep learning system has been trained, it can be provided to other computing systems without retraining. In some examples, the executable instructions 110 may be used to generate hardware to implement some or all of the deep learning system (e.g., ASIC) which may be provided to one or more computing systems for implementing the deep learning system.

Training, validation, and testing data for the example implementation of deep learning system described herein were acquired from the Osteoarthritis Initiative (OAI). A total of 176 3D sagittal double-echo in steady-state (DESS) datasets from the OAI were utilized for training. All images had dual-knee weight-bearing radiographs to analyze Kellgren-Lawrence (KL) osteoarthritis grade.

For training, thick slice images were simulated from the training set of thin slice images. The ratio of the ground-truth slice thickness and the downsampled low-resolution slice thickness is referred to as downsampling factor (DSF). Thick-slice representation of the high-resolution thin-slice images was generated by anti-aliasing filtering and consequent downsampling of the thin-slice images in the left-right direction. A 1D finite impulse response, low-pass, 48th-order Hamming-windowed filter with a normalized passband of 1/DSF was generated in for the retrospective downsampling. This simulated acquisition of thicker slices that have magnetization contributions from surrounding slices. The training dataset of the example implementation includes the ground-truth high-resolution images and the simulated low-resolution images. The low-resolution images may be upscaled using 1D tricubic interpolation (TCI) in the slice direction (left-right) at the ground-truth slice locations in some examples. However, other methods of obtaining thick slice images may be used. For example, a data set including thin slice images and thick slice images acquired from a same volume may be used to train the deep learning system.

Other datasets of varying resolutions may be used in other examples. A training data set for processing a particular feature may include previous images of patients having the feature. For example, in gastrointestinal imaging, volume images of livers and/or livers including a lesion-type of interest may be used to train the deep learning system to generate improved resolution images of the liver.

In some examples, training data may be pre-processed prior to training the deep learning system. Pre-processing the training data may improve the training process and result in a better trained deep learning system in some applications. Pre-processing may include formatting the data to ensure uniform size, cropping images to include only relevant anatomy, uniform scaling of intensity values, and/or subdivided into patches.

Accordingly, deep learning systems described herein may be trained using high resolution images (e.g., "ground truth images") and simulated low-resolution images based on those high resolution images. The simulated low-resolution images may be downsampled versions of the high resolution images. In some examples, after being downsampled, the images may be interpolated such that the simulated low-resolution images are a same or similar size as the high resolution images (e.g., "ground truth images"). In this manner, a set of simulated low-resolution images are provided which have a known association with a set of high-resolution images. Deep learning systems described herein may be trained (e.g., coefficients and other parameters for operation of the deep learning system may be selected) on the set of simulated low-resolution images. A set of coefficients and other parameters may be selected which generally provide an accurate output of the "ground truth images" from the simulated low-resolution images.

Figure 5:
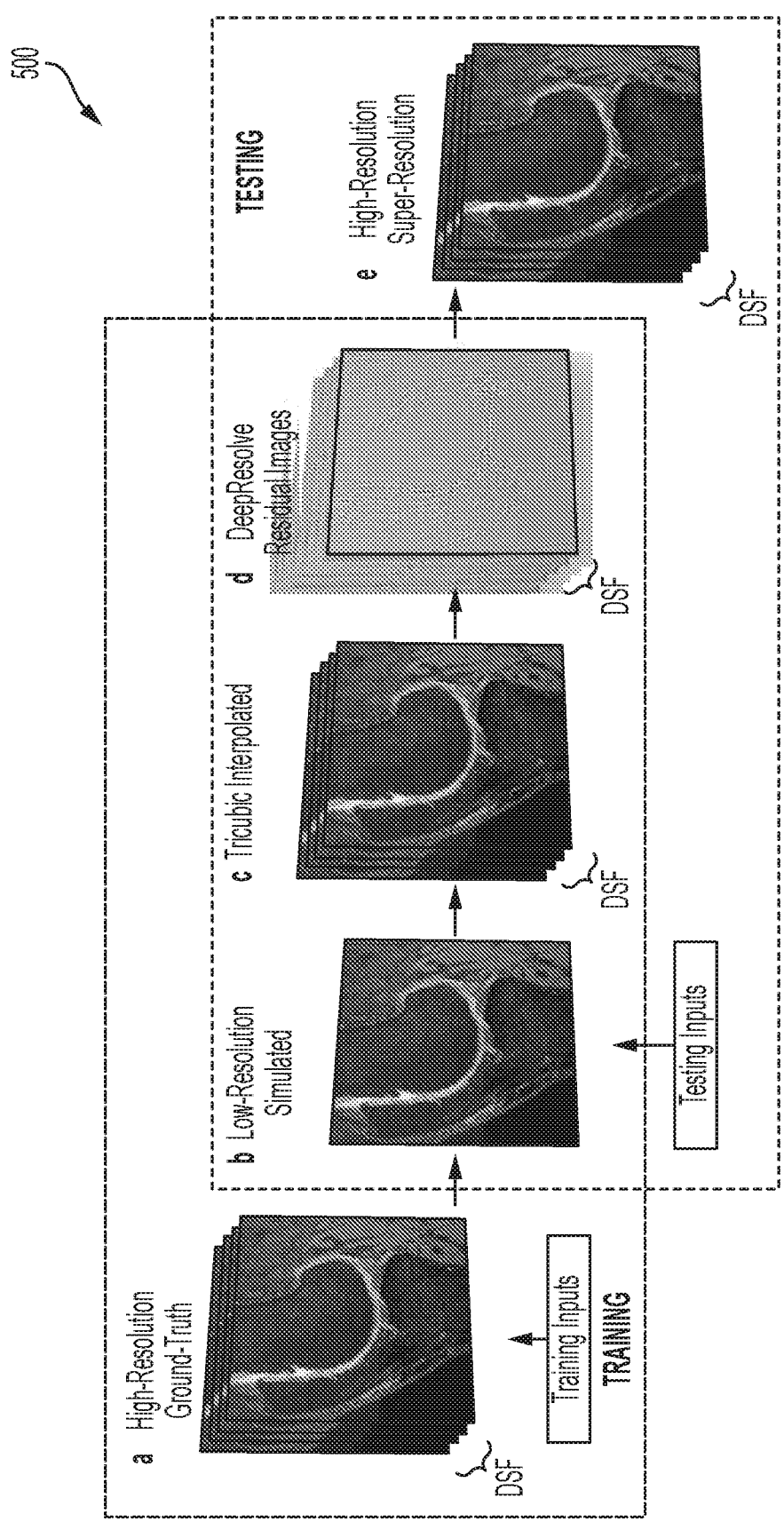
FIG. 5 shows an example workflow of implementing a neural network in accordance with examples described herein.

FIG. 5 illustrates an example workflow 500 in accordance with examples of the present disclosure. In the example implementation, high-resolution ground-truth slices (a) were used to simulate acquisition of slices with a higher section thickness (b) for varying downsampling factors (DSFs). These slices were subsequently tricubicly interpolated to the ground-truth slice locations (c) and the deep learning system training identified a residual function (d) that can be added to the low-resolution thick-slices to produce the high-resolution thin-slices (e). During inference, a residual image is created for the testing input using the learned residual model. Consequently, the residual can be added to the low-resolution input in order to output a super-resolution image. In other words, the deep learning system may receive thick slice images as inputs and generate simulated thin slice images as outputs. The deep learning system may allow for fewer image slices to be acquired while still maintaining adequate resolution for diagnostic purposes in some applications. This may allow for a reduction in patient imaging time in some applications, which may in turn improve patient comfort and/or reduce exposure to ionizing radiation.

Figure 6:
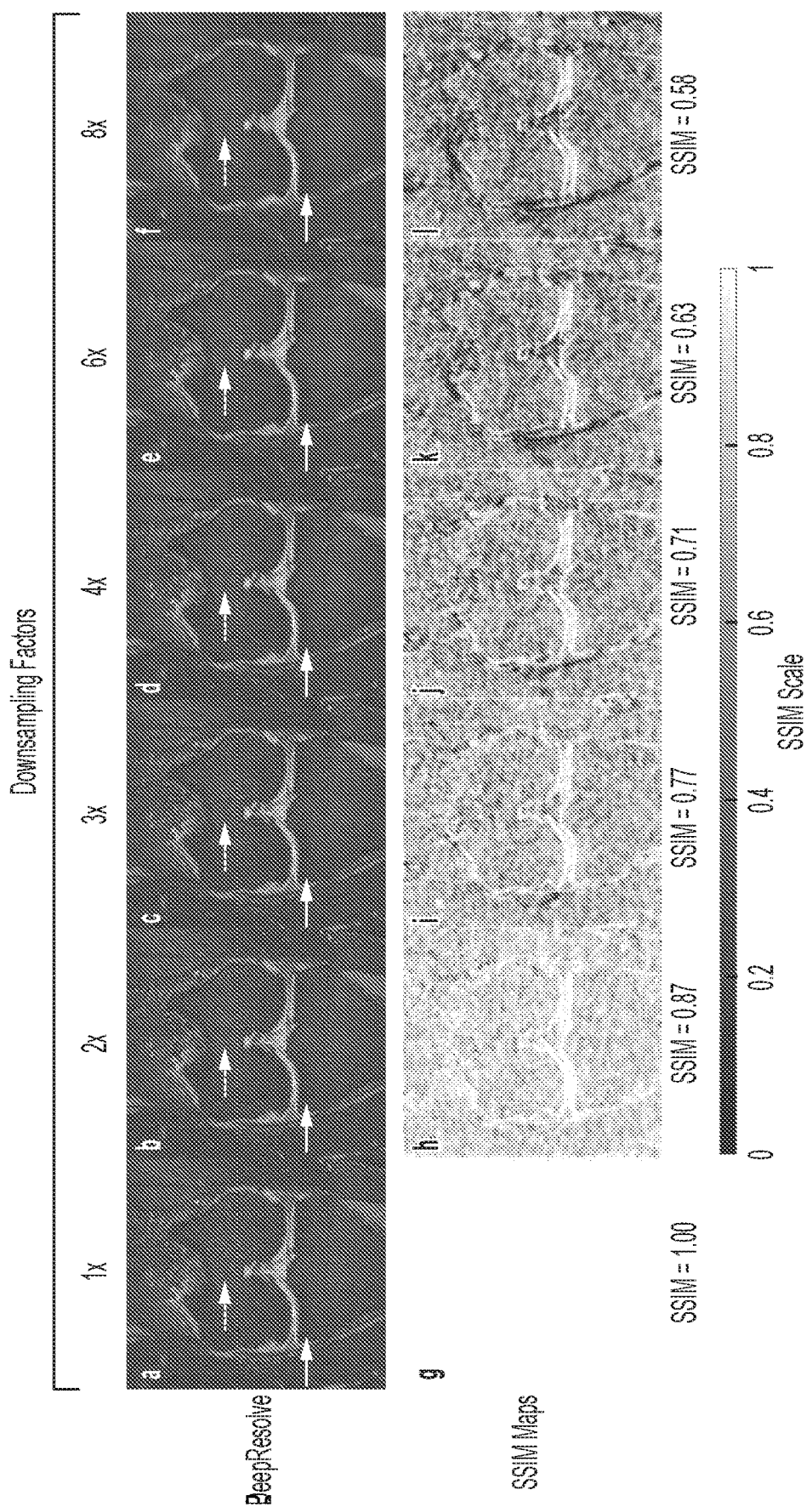
FIG. 6 is exemplary coronal images with varying downsampling factors and corresponding 2D structural similarity maps in accordance with examples described herein.

FIG. 6 illustrates exemplary coronal deep learning images with varying downsampling factors (DSFs) (panes a-f) and corresponding 2D structural similarity (SSIM) maps (panes g-l) in accordance with examples of the present disclosure. The deep learning images and SSIM maps may be compared to the ground-truth slice (e.g., the actually acquired thin slice image). While images with a higher DSF may be over-smoothed, the directionality of the blurring is also more apparent. In the femoral bone marrow, pixels with imperfect fat-saturation appear more blurred in the left-right direction, than in the inferior-superior direction (dotted arrow). The medial collateral ligament may be a tissue to illustrate image fidelity in the coronal reformation since it is very thin in the left-right direction (solid arrow). The SSIM maps illustrate that the MCL is not reproduced with high diagnostic quality for DSFs of 6 and 8. The coronal images with varying DSFs and their SSIM maps indicated that as the DSF was increased, fine details of the medial collateral ligament (MCL) and the anterior cruciate ligament (ACL) were blurred out (arrows on SSIM maps). Moreover, the remnant femoral bone marrow signal due to imperfect fat-suppression, appeared overly-smoothed, which decreased the local SSIM. In this example, the sagittal images were least affected by blurring as the DSF increased, while the axial and coronal reformations showed higher blurring with increasing DSFs.

Figure 7:
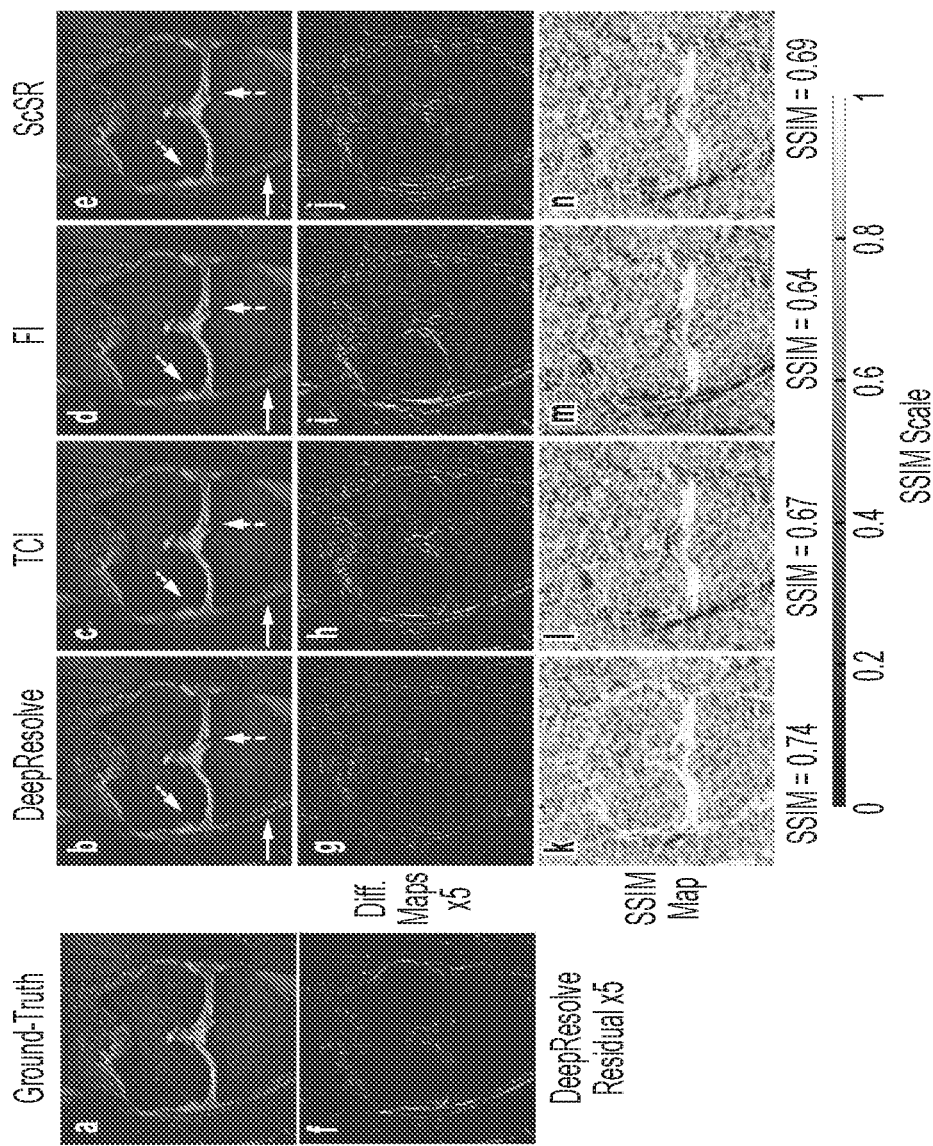
FIG. 7 illustrates a comparison of an example embodiment of the disclosure with other resolution-enhancement techniques.

A comparison of the example implementation of the deep learning system to other super-resolution methods including TCI, FI, and ScSR methods for a DSF of 3×, and the ground-truth images, is shown in FIG. 7. An example coronal ground-truth image (pane a) and the resolution-enhanced images with a downsampling factor (DSF) of 3× at the same slice location used for (pane b) DeepResolve, (pane c) Fourier interpolation (FI), (pane d) tricubic interpolation (TCI), and (pane e) sparse-coding super-resolution (ScSR). The deep learning system-generated residual map (pane f) as well difference images (e.g., difference maps), scaled by a factor of 5 to accentuate subtle differences, between the comparison methods and the ground-truth image are shown (panes g-j). The corresponding 2D structural similarity (SSIM) maps for the resolution-enhanced images compared to the ground-truth are also shown (panes k-n). The deep learning system of the present disclosure maintained fine features in the coronal reformation and was most comparable in terms of qualitative visual quality and quantitative structural similarity measures to the original ground-truth image. High-resolution features such as the MCL (solid arrow), a small osteophyte on the lateral tibial plateau (dashed arrow), and inflammation with sharp features (dotted arrow) were easily visualized on the deep learning system image, however, visualization was far more challenging with the other methods (a-e). This was further indicated through the difference maps (g-j) and pixel-by-pixel structural similarity maps (k-n) where unlike the deep learning system of the present disclosure. TCI, FI, and ScSR all had lower similarity around the medial collateral ligament.

The deep learning system described herein may provide the ability to diagnose subtle pathologies from thick slices. For example, three pairs of artificial meniscal and cartilage lesions with varying signal intensity were simulated and lesions were manually created that were subtle spatially and in signal intensity.

Figure 8:
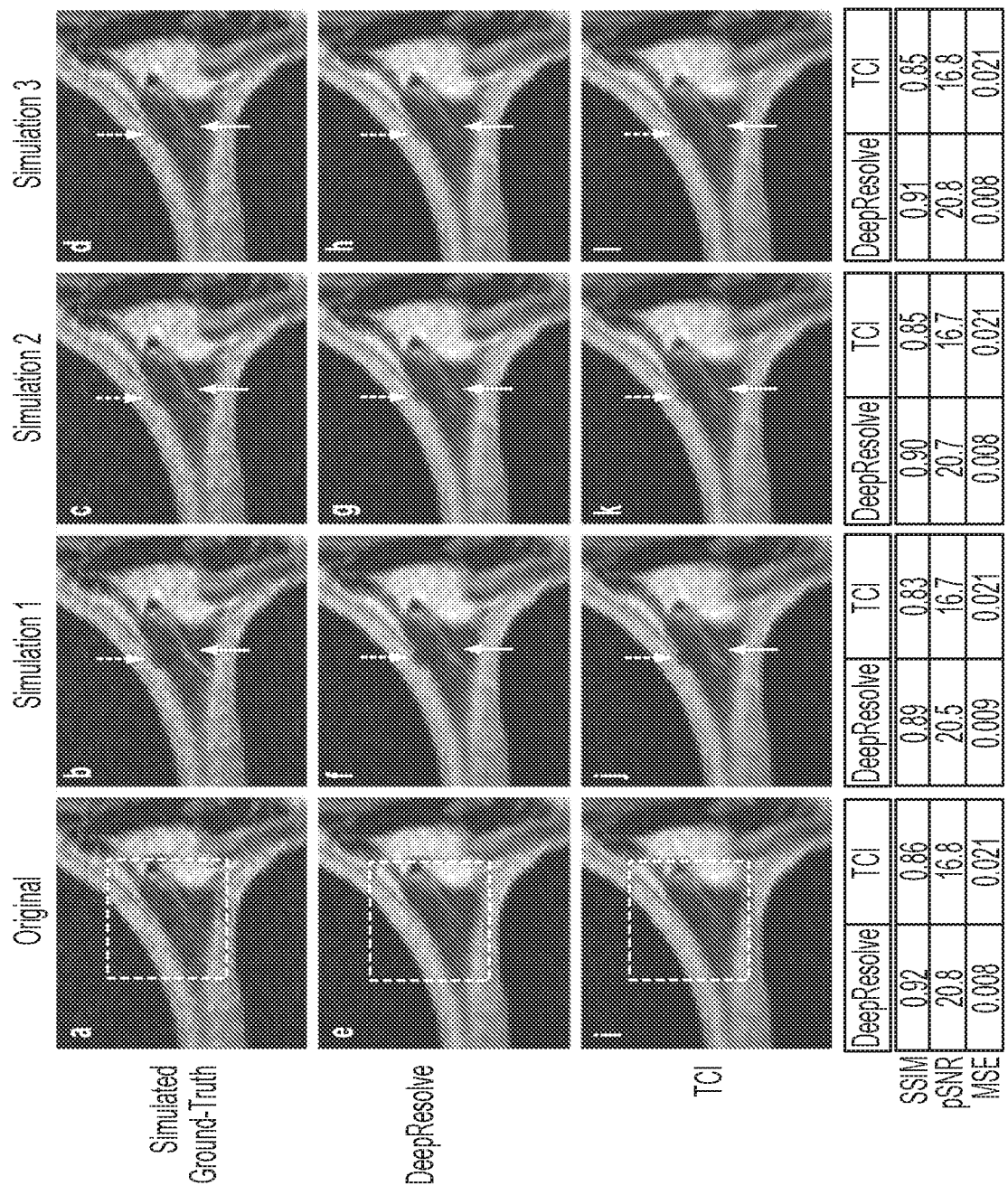
FIG. 8 is a set of simulated ground-truth images and resulting generated images in accordance with examples described herein.

FIG. 8 shows the simulated ground-truth images and resulting generated images according to examples of the present disclosure. The ground-truth image (pane a) was modified to include artificial meniscal lesions (solid arrow) and cartilage lesions (dotted arrow) of varying signal intensities (panes b-d). The simulated meniscal tear was only two pixels thick in the horizontal and vertical direction. With the ground-truth simulations as an input, a DSF of 3× demonstrated that the deep learning system (panes e-h) reproduced the lesions moderately well and had lower blurring than TCI images (panes i-l). The deep learning system of the present disclosure consistently had better similarity metrics (higher SSIM and pSNR, lower MSE) with respect to the ground-truth than TCI.

Figure 9:
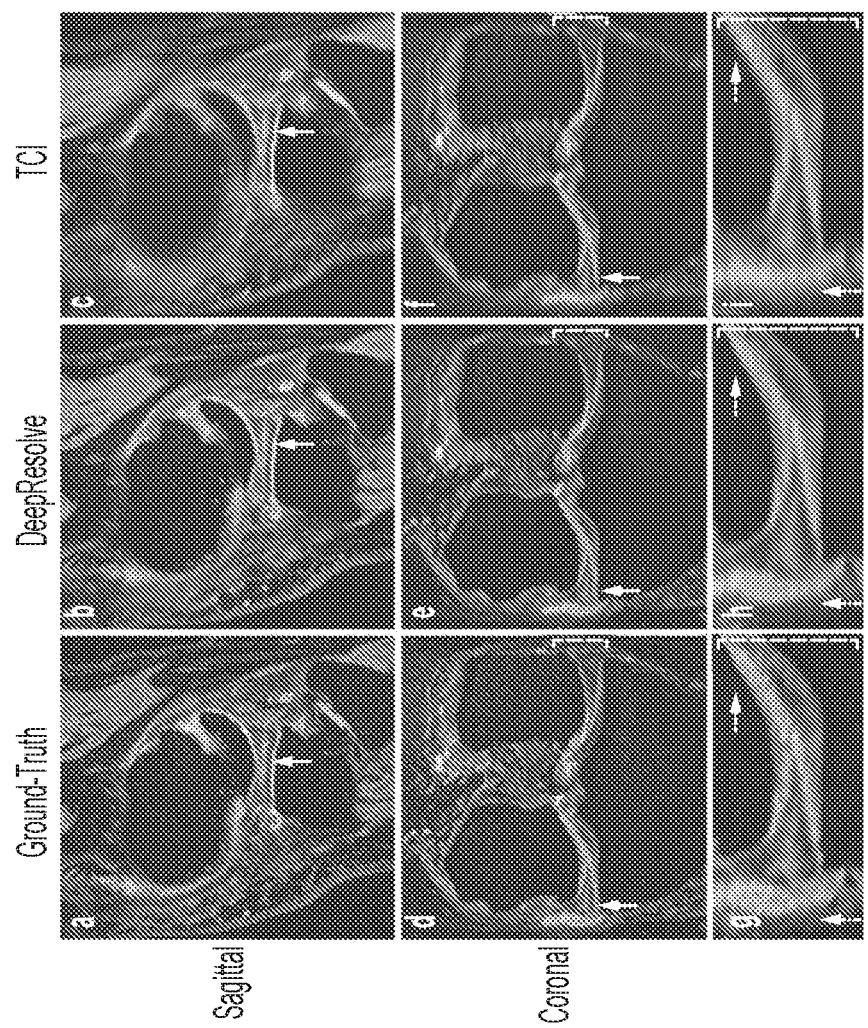
FIG. 9 shows example images of a horizontal tear in the body of the lateral meniscus in accordance with examples described herein.

The example images of FIG. 9 show an example of a horizontal tear in the body of the lateral meniscus that can be identified with the hyperintense DESS signal. The tear (arrow) can be seen relatively similarly in the sagittal ground-truth, DeepResolve, and TCI images (pane a-c). However, there is some blurring evident in the posterior femoral cartilage which overestimated the cartilage thickness. The coronal reformation also indicates the same meniscal tear (pane d-f). A zoomed section of the coronal image (yellow bracket) shows that the deep learning system image appears more smoothed and less noisy than the ground-truth image (pane g-i). Comparing the TCI image to both the ground-truth and deep learning system images shows considerably more blurring in the TC image. The border of the inflammation (green arrow) in the TCI image does not have the same contours as the ground-truth while the central cartilage has a stair-like jagged appearance (dotted arrow) instead of smooth edges.

Figure 10:
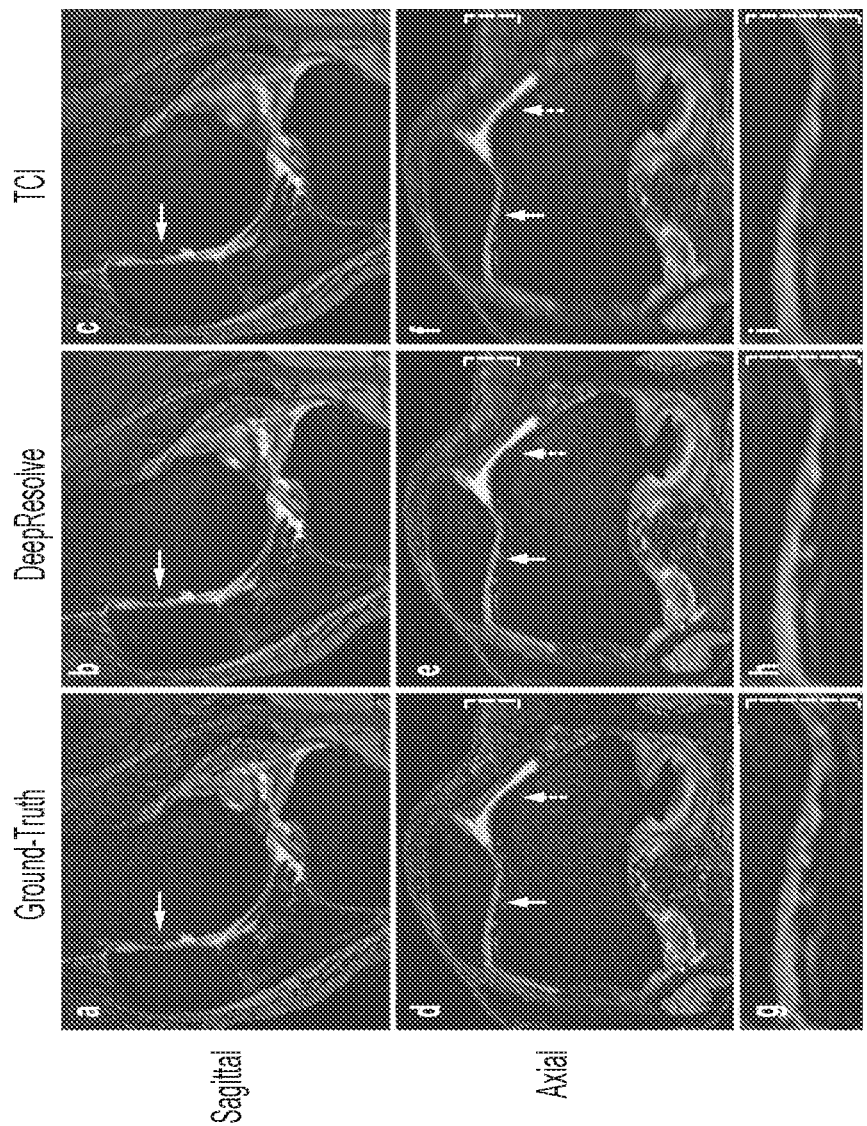
FIG. 10 shows example images of a subtle case of grade 2A chondromalacia of the lateral patellar cartilage in accordance with examples described herein.

The example images of FIG. 10 show an example of a subtle case of grade 2A chondromalacia of the lateral patellar cartilage was identified with a hypointense DESS signal. The cartilage (indicated with arrows) appears similar on all three sagittal images. However, the axial reformations demonstrate the slightly higher fidelity of the deep learning system images compared to the TCI images (pane a-c). The joint effusion (dotted arrows) on the axial images around the lateral femoral condyle appears with a very jagged appearance on the TCI images compared to the ground-truth and deep learning system (pane d-f). The zoomed section of the axial reformations shows contours of the patellar cartilage and the heterogeneous signal maintained better in the deep learning system images than TCI images, but not as well as the ground-truth images (pane g-i).

An example of a meniscus tear of the lateral body for all three sets of images showed that the sagittal TCI image exhibited more blurring than the deep learning system image, however, the coronal TCI reformation was considerably blurrier than deep learning system of the present disclosure. Contours of fine structures such as the cartilage, meniscus, and the joint inflammation in the deep learning system images appeared more comparable to the ground-truth images. In contrast to the gross meniscal tear, a very subtle finding of a grade 2A lateral patellar chondromalacia (according to a modified Noyes scale) appeared similarly on all three sagittal image-sets, but the axial deep learning system reformations had better image quality than TCI. The fine contours of the cartilage and the chondral signal heterogeneity were adequately depicted on the ground-truth image but appeared blurrier on deep learning system and TCI images. However, the deep learning system of the present disclosure did maintain higher image quality than TCI. As illustrated in FIGS. 8-10 deep learning system of the present disclosure has potential for diagnostic use. For example, a healthy MCL usually has sub-millimeter thickness in the coronal plane and the deep learning system was able to maintain fine MCL detail in an acquisition that simulated a slice thickness of 2.1 mm. In another example, meniscal tears and fine cartilage lesions are visible in images generated by the deep learning system of the present disclosure. In some applications, the deep learning system may be used for clinical use for acquiring slices at 2-3 mm slice thicknesses and subsequently transforming them into thinner slices (e.g., higher resolution) for multi-planar reformations. Such methods could also be especially useful for newer implementations of DESS that enable simultaneous $T_2$ relaxometry, morphometry, and semi-quantitative radiological assessment. For example, the thicker slices could be used for generating high-SNR for quantitative $T_2$ measurements, while the thin slices could be used for accurate morphometry and semi-quantitative whole-joint assessment in some applications. Bilateral knee imaging methods that acquire several hundred slices could also benefit from the deep learning system of the present disclosure.

Figure 11:
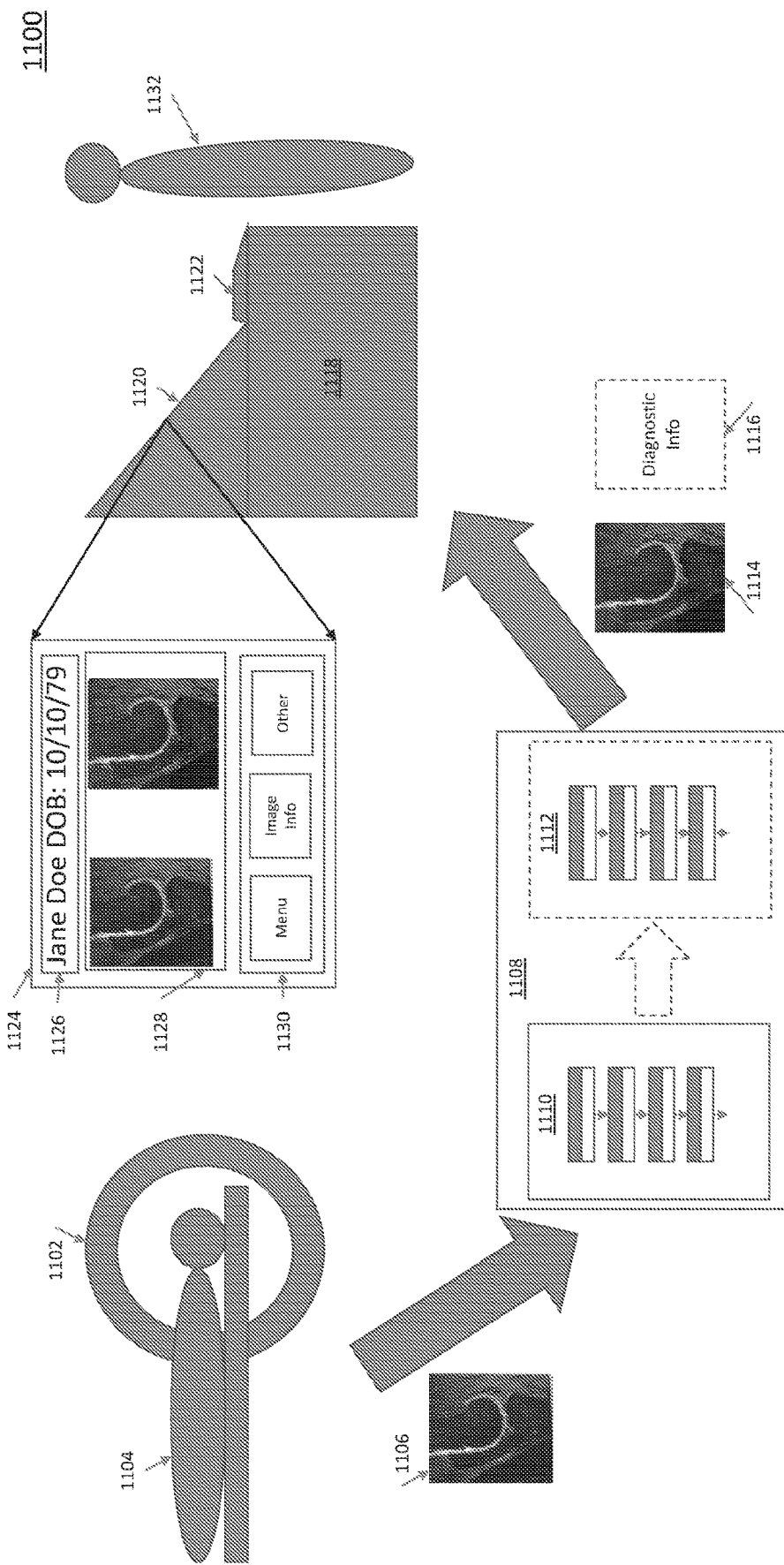
FIG. 11 is an illustration of a system arranged in accordance with examples described herein.

FIG. 11 is an illustration of a system 1100 arranged in accordance with examples described herein. The system 1100 may include an image acquisition unit 1102, a computing system 1108, and a work station 1118. In some embodiments, the image acquisition unit 1102, computing system 1108, and work station 1118 may be integrated as a single unit.

In some examples, the image acquisition unit 1102 may be a magnetic resonance imaging (MRI) imaging system. In some examples, the image acquisition unit 1102 may be a computed tomography (CT) imaging system. In some examples, the image acquisition unit 1102 may be an ultrasound (US) imaging system. In some examples, the image acquisition unit 1102 may be another imaging modality capable of acquiring image slices of a finite thickness. The image acquisition unit 1102 may acquire one or more image slices 1106 from a subject 1104. The subject 1104 may be a human or animal subject. The image slices 1106 may include one or more features of interest in some examples. The feature of interest may be an anatomical feature in some examples. In the example shown in FIG. 11, image slice 1106 includes a knee joint. The image slices 1106 may be provided to computing system 1108 in some examples.

In some examples, the computing system 1108 may be implemented by computing system 106 shown in FIG. 1. The computing system 1108 may include one or more memories (not shown) capable of storing executable instructions and one or more processors (not shown) capable of executing the executable instructions. The one or more memories may be configured to store the one or more image slices 1106 provided by the image acquisition unit 1102. The computing system 1108 may be configured to implement a deep learning system 1110. The deep learning system 1110 may be configured to generate high resolution (e.g., thin slice) images 1114 from the image slices 1106. In some examples, the deep learning system 1110 may be implemented by deep learning system 200 shown in FIGS. 2-4. The high resolution images 1114 may be provided to the work station 1118. In some examples, the computing system 1108 may be included in the work station 1118. In some examples, the computing system 1108 may be remote from the work station 1118 and may communicate with the work station 1118 via a network interface (e.g., network interface 116 shown in FIG. 1).

Optionally, in some examples, computing system 1108 may be configured to implement a second deep learning system 1112. The second deep learning system 1112 may be configured to receive the high resolution images 1114 and output diagnostic information 1116. The deep learning system 1112 may be trained to recognize anatomical features in the high resolution images 1114 associated with one or more pathologies (e.g., torn meniscus) and output diagnostic information 1116 associated with the recognized pathologies. However, other deep learning systems may be used to implement deep learning system 1112 in other examples. The diagnostic information 1116 may be provided to the work station 1118.

Workstation 1118 may include a display 1120 and a user interface 1122. An example of data that may be provided on the display 1120 is shown in box 1124. In some examples, the display 1120 may provide subject information 1126. Subject information may include name, birthdate, identification number, and/or other information. In some examples, the display 1120 may provide the image slice 1106 and/or the high resolution image 1114. In some examples, the display 1120 may provide multiple image slices 1106 and/or the high resolution images 1114 simultaneously. In some examples, the display 1120 may provide a variety of other information 1130 such as a menu of options (e.g., editing images, saving images, acquiring measurements from images), information regarding the images displayed (e.g., image acquisition unit 1102 settings, anatomical view of slices 1106, 1114), and/or other information (e.g., diagnostic information 1116, physician notes).

Work station 1118 may include a user interface 1122. The user interface 1122 may include any type of hard and/or soft user controls. Examples of hard user controls include, but are not limited to, keyboard, trackball, mouse, and switches. Examples of soft user controls include, but are not limited to, a touch screen with software-implemented graphical buttons, sliders, and/or toggles. The user interface 1122 may be configured to receive user inputs from a user 1132. For example, the user inputs may determine when image slices 1106 are acquired and/or under what conditions (e.g., thickness). In another example, the user inputs may determine what images are displayed on display 1120.

In some applications, the deep learning systems described herein, such as deep learning system 1110 may permit an image acquisition unit, such as image acquisition unit 1102 to acquire fewer slices, such as slices 1106, of a volume of a subject 1104 while still providing diagnostic-quality images, such as high resolution images 1114. This may improve the functioning of the image acquisition unit by reducing image acquisition time. In some applications, the deep learning systems described herein may improve the resolution of the slices acquired by an image acquisition unit. For example, image acquisition unit 1102 may acquire a number of thin image slices 1106 of a volume. The deep learning system 1110 may enhance the resolution of the thin image slices 1106 by simulating even thinner slice (e.g., higher resolution) images 1114.

Users of deep learning systems described herein, such as user 1132, may use outputs of the deep learning systems, such as high resolution images 1114, to make a diagnosis of a subject, such as subject 1104. For example, a physician may be able to diagnose a chondromalacia of the lateral patellar cartilage and/or stage osteoarthritis based on the features of interest (e.g., knee) visible in high resolution images 1114. The user 1132 may further make treatment determinations based on the diagnosis from the high resolution images 1114. Example of treatment options include, but are not limited to, surgery, physical therapy, and a supportive brace. In some examples, the diagnosis and/or treatment determination may not be possible based on the originally acquired image slices 1106.

In summary, a deep learning system as described herein may be capable of resolving high-resolution thin-slice features from slices originally considerably thicker. In other words, the deep learning system generates images where each voxel represents less volume than voxels in the originally acquired images. It is to be understood that while the example implementation used musculoskeletal MRI other examples of deep learning systems, and other modalities of images (such as brain MRI or CT) may also be used. Additionally, the deep learning system could be used to enhance resolution in all three dimensions. The deep learning system may be implemented on one or more computer systems—e.g., systems having one or more processing units (e.g., processors such as central processing units (CPUs) and/or graphics processing units (GPUs) and computer readable media (e.g., memory, storage) encoded with executable instructions for performing the deep learning techniques and/or training described herein.

From the foregoing it will be appreciated that, although specific embodiments have been described herein for purposes of illustration, various modifications may be made while remaining with the scope of the claimed technology.

What is claimed is:

1. A method of generating thin slice images from thick slice images, the method comprising:
receiving a first image having a first resolution at a neural network;
performing a convolution on the first image with the neural network;
performing a non-linear activation function on the first image with the neural network;
repeating the convolution and non-linear activation function;
generating a residual based on the convolution; and
summing the residual and the first image with the neural network to generate a second image having a second resolution, wherein the second resolution is higher than the first resolution.

2. The method of claim 1, wherein the performing the convolution and performing the non-linear activation function are performed and repeated in a plurality of layers of the neural network, wherein the first image is an input of a first layer of the plurality of layers, an output of the first layer of the plurality of layers is an input of a second layer of the plurality of layers, and an output of a last layer of the plurality of layers is the residual.

3. The method of claim 1, further comprising training the neural network on a training data set, wherein the training data set includes a plurality of first images and a plurality of second images.

4. The method of claim 1, further comprising testing the neural network on a testing data set, wherein the testing data set includes a plurality of first images.

5. The method of claim 1, wherein performing the convolution includes performing a three dimensional convolution.

6. The method of claim 1, wherein training the neural network includes dividing the first images into a plurality of pixel patches.

7. The method of claim 1, wherein the non-linear activation function includes a form of R(x)=max(0,x).

8. The method of claim 1, further comprising acquiring the first image from an imaging system.

9. The method of claim 8, wherein the imaging system is a magnetic resonance imaging system.

10. A system for generating thin slice images from thick slices images, the system comprising:
a non-transitory computer readable medium including instructions for implementing a neural network, wherein the neural network comprises a level including a convolution block and a rectified linear unit non-linear activation block, wherein the level is configured to generate a residual from a first image having a first resolution received by the neural network, wherein the neural network is configured to sum the first image and the residual to generate a second image having a second resolution, wherein the second resolution is higher than the first resolution; and
a processor configured to execute the instructions to implement the neural network.

11. The system of claim 10, further comprising a display configured to display the second image.

12. The system of claim 10, wherein the convolution block applies a three dimensional convolution and thresholding using rectified linear unit function to the first image.

13. The system of claim 10, wherein the neural network includes a plurality of levels, wherein an output of a first level of the plurality of levels is provided as an input to a second level of the plurality of levels.

14. The system of claim 13, wherein a last level of the plurality of levels does not include the rectified linear unit non-linear activation block.

15. The system of claim 13, wherein a last level of the plurality of levels has a dimension less than others of the plurality of levels.

16. The system of claim 10, wherein the neural network divides the first image into a plurality of pixel patches.

17. The system of claim 16, wherein the plurality of pixel patches overlap.

18. The system of claim 17, wherein the plurality of pixel patches overlap by 50%.

19. The system of claim 10, wherein the convolution block applies a zero- padded convolution and an output of the zero-padded convolution is cropped to an original size of the input image.

20. The system of claim 10, wherein the convolution block outputs a plurality of feature maps.

21. A system for generating high resolution images from low resolution images, the system comprising:
an image acquisition unit configured to acquire a first image of a feature of interest at a first resolution;
a computing system configured to implement a deep learning system, wherein the deep learning system is configured to receive the first image of the feature of interest and, perform a convolution on the first image, perform a non-linear activation function on the first image, repeat the convolution and non-linear activation function, generate a residual based on the convolution, and sum the residual and the first image to generate a second image of the feature of interest at a second resolution, wherein the second resolution is higher than the first resolution; and
a display configured to display the second image of the feature of interest.

22. The system of claim 21, wherein the image acquisition unit is a magnetic resonance imaging system.

23. The system of claim 21, wherein the deep learning system generates the second image by supplementing the first image.

24. The system of claim 21, wherein the computing system is configured to implement a second deep learning system and the second image of the feature of interest is provided as an input to the second deep learning system.

\* \* \* \* \*